(12) United States Patent
Angelescu et al.

(10) Patent No.: US 8,262,909 B2
(45) Date of Patent: *Sep. 11, 2012

(54) METHODS AND DEVICES FOR MINIMIZING MEMBRANE FOULING FOR MICROFLUIDIC SEPARATORS

(75) Inventors: Dan Eugen Angelescu, Somerville, MA (US); Philippe Salamitou, Paris (FR); Joyce Wong, Pasadena, CA (US); Bhavani Raghuraman, Wilton, CT (US); Brian Oliver Clark, Sugar Land, TX (US); Christopher Harrison, Auburndale, MA (US); Matthew Sullivan, Westwood, MA (US); Andreas Hausot, Tokyo (JP); Florence Le Gallic de Kerizouet, Vannes (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 467 days.

This patent is subject to a terminal disclaimer.

(21) Appl. No.: 12/503,650

(22) Filed: Jul. 15, 2009

(65) Prior Publication Data

US 2010/0012586 A1   Jan. 21, 2010

Related U.S. Application Data

(63) Continuation-in-part of application No. 10/935,858, filed on Sep. 8, 2004, now Pat. No. 7,575,681, which is a continuation-in-part of application No. 10/885,471, filed on Jul. 6, 2004, now Pat. No. 7,799,278.

(51) Int. Cl.
*B01D 63/00* (2006.01)
*B01D 11/00* (2006.01)

(52) U.S. Cl. ............. 210/321.75; 210/321.6; 210/257.2; 422/10; 422/72; 422/101; 166/308.3

(58) Field of Classification Search ............. 210/321.75, 210/321.6, 257.2, 170.01; 166/308.3, 380, 166/302; 422/72
See application file for complete search history.

(56) References Cited

U.S. PATENT DOCUMENTS 5,116,759 A    5/1992   Klainer et al.
(Continued)

FOREIGN PATENT DOCUMENTS

DE    19941271 A1    4/2001
(Continued)

OTHER PUBLICATIONS

Combined Search and Exam Report of British Application Serial No. 0518160.7 dated Dec. 1, 2005 (Report completed Nov. 30, 2005).
(Continued)

*Primary Examiner* — Ana Fortuna (57) ABSTRACT

A fluid separation method for performing fluid analysis of an unfiltered fluid. The fluid separation method includes providing a structure with a fluid analyzer and a power supply. Using a substrate for receiving a fluid flow stream of a multiphase mixture through a fluid sample inlet, wherein the substrate interconnects with the structure. Providing a membrane disposed across the fluid sample inlet for separating a fluid of interest from the multiphase mixture, wherein the fluid flow stream of the multiphase mixture has a shear rate that prevents a fouling of the membrane. Finally, the fluid separation method includes the substrate having fabricated channels, such that the fabricated channels are arranged substantially tangent to the fluid stream downstream of the porous membrane.

41 Claims, 8 Drawing Sheets

U.S. PATENT DOCUMENTS

| | | | |
|---|---|---|---|
| 5,300,228 | A | 4/1994 | Sugaya et al. |
| 5,645,725 | A | 7/1997 | Zitzelsberger et al. |
| 5,984,021 | A * | 11/1999 | Pascale ............ 173/90 |
| 5,984,023 | A | 11/1999 | Sharma et al. |
| 6,039,897 | A | 3/2000 | Lochhead et al. |
| 6,074,827 | A | 6/2000 | Nelson et al. |
| 6,262,519 | B1 | 7/2001 | Furlani et al. |
| 6,306,590 | B1 | 10/2001 | Mehta et al. |
| 7,231,819 | B2 * | 6/2007 | Jones et al. ............ 73/152.23 |
| 7,264,723 | B2 * | 9/2007 | Singh et al. ............ 210/321.6 |
| 7,323,140 | B2 | 1/2008 | Handique et al. |
| 7,332,126 | B2 | 2/2008 | Tooke et al. |
| 7,351,376 | B1 * | 4/2008 | Quake et al. ............ 422/504 |
| 7,378,280 | B2 * | 5/2008 | Quake et al. ............ 436/63 |
| 7,390,463 | B2 * | 6/2008 | He et al. ............ 422/504 |
| 7,575,681 | B2 * | 8/2009 | Angelescu et al. ...... 210/321.74 |
| 7,695,629 | B2 * | 4/2010 | Salamitou et al. ............ 210/650 |
| 7,799,278 | B2 | 9/2010 | Salamitou et al. |
| 2002/0164816 | A1 | 11/2002 | Quake |
| 2002/0187074 | A1 | 12/2002 | O'Connor et al. |
| 2003/0106799 | A1 | 6/2003 | Covington et al. |
| 2003/0150791 | A1 | 8/2003 | Cho et al. |
| 2004/0129874 | A1 | 7/2004 | Torgersen et al. |

FOREIGN PATENT DOCUMENTS

| | | |
|---|---|---|
| EP | 1614465 B1 | 8/2007 |
| JP | 2003190768 | 7/2003 |
| WO | 0020117 A2 | 4/2000 |
| WO | 02077613 A2 | 10/2002 |
| WO | 2004087283 A1 | 10/2004 |

OTHER PUBLICATIONS

Search Report of European Application Serial No. 05076524.7 dated Sep. 27, 2005.

Anonymous, "106 Oil-Water Separation," GE Infrastructure Water & Process Technology, retrieved Jun. 13, 2005: 1 page, <http://www.gewater.com/library/tp/221_106_Oil-Water.jsp>.

Jr-Hung Tsai et al., "Active microfluidic mixer and gas bubble filter driven by thermal bubble micropump," Sensors and Actuators, 2002, vol. A97-98: pp. 665-671.

Abraham D. Stroock et al., "Chaotic Mixer for Microchannels," Science, Jan. 2002, vol. 295: pp. 647-651.

Neena Pradhan Tirmizi et al., "Demulsification of Water/Oil/Solid Emulsions by Hollow-Fiber Membranes," AIChE Journal, May 1996, vol. 42(5): pp. 1263-1276.

J. Cooper McDonald et al., "Fabrication of microfluidic systems in poly(dimethylsiloxane)," Electrophoresis, 2000, vol. 21: pp. 27-40.

Anonymous, "Fiber Optic pH Sensors," Ocean Optics Product Catalog on Spectrometers and Accessories, 2004, p. 58.

Jaromír Růžička et al., "Flow Injection Analysis," Chemical Analysis vol. 62, eds. Elving et al., New York: John Wiley & Sons, 1981: pp. 1-30.

S. C. Terry, "A Gas Chromatography System Fabricated on a Silicon Wafer Using Integrated Circuit Technology," PhD Thesis, Stanford University, 1975.

Anonymous, "Low Flow Pumping Technology," Micropump Inc., 2004, retrieved Jun. 13, 2005, 1 page, <http://wwww.micropump.com>.

Anonymous, "Microfiltration Media," GORE Creative Technologies Worldwide, W. L. Gore & Associates, Inc., 2005, retrieved Jul. 7, 2005, 2 pages, <http://www.gore.com/en_xx/products/filtration/micro/index.html>.

Elisabeth Verpoorte et al., "Mlcrofluidcs Meets MEMS," Proceedings of the IEEE, Jun. 2003, vol. 91(6): pp. 930-953.

A. Manz et al., "Miniaturized Total Chemical Analysis Systems: a Novel Concept for Chemical Sensing," Sensors and Actuators, 1990, vol. B1: pp. 244-248.

Anonymous, "3000 Micro GC—The Power is in Your Hands . . . ," Agilent Technologies, 2000-2004, retrieved Jun. 13, 2005: pp. 1-3, <http://www.chem.agilent.com/scripts/pds.asp?1Page=1916>.

Anonymous, "Product Information: Flat Sheet Membranes Data Sheets: Celgard 2320 Microporous Membrane," Celgard Inc., retrieved Jun. 13, 2005, 2 pages, <http://www.celgard/products/product-information.cfm>.

Anonymous, "Films, P/S Tapes, Specialty," DeWal.com, retrieved Jun. 13, 2005, 1 page, <http://www.dewal.com/productline.cfm>.

Arthur I. Vogel, "Chapter X: Colorimetric and Spectrophotometric Analysis," A Text-Book of Quantitative Inorganic Analysis Including Elementary Instrumental Analysis, New York: John Wiley and Sons Inc., 1961: pp. 738-781.

Anonymous, "The small thinXXS in life . . . ," thinXXS Microtechnology: micro pump, microfluidics, micromolding, and more, retrieved Jun. 13, 2005, 1 page, <http://www.thinxxs.com/>.

* cited by examiner

METHODS AND DEVICES FOR MINIMIZING MEMBRANE FOULING FOR MICROFLUIDIC SEPARATORS

This patent application claims priority from U.S. patent application Ser. No. 10/885,471 filed Jul. 6, 2004, incorporated by reference herein in its entirety. This patent application is a continuation-in-part from U.S. patent application Ser. No. 10/935,858, now U.S. Pat. No. 7,575,681, filed Sep. 8, 2004 (U.S. patent application Ser. No. 10/935,858 filed Sep. 8, 2004 is a continuation-in-part from U.S. patent application Ser. No. 10/885,471, now U.S. Pat. No. 7,799,278, filed Jul. 6, 2004), is incorporated by reference herein in its entirety.

BACKGROUND OF THE INVENTION

1. Field of the Invention

The present invention relates to methods and devices for minimizing membrane fouling for microfluidic separators. In particular, methods and devices related to minimizing filter cake build-up on a membrane exposed to live oilfield fluids downhole.

2. Background of the Invention

The ability to reliably separate a fluid of interest can be very beneficial for oilfield, medical, biological, and analytical chemistry applications. Fluids of interest may include water, oil, gas, or other fluids. Separating fluids of interest enables specific measurements to be performed on the particular fluid. For example, pH and various ion concentrations may be measured if the fluid of interest is water. For oil, near-infrared absorption spectroscopy may be performed to detect various light-weight hydrocarbons, and other types of chromatography may be used to detect detailed chemical composition.

However, in order to perform accurate measurements on the fluid of interest, the fluid of interest must be separated from other components prior to taking the measurements. A major problem in accomplishing the separation of other components includes fouling or clogging of the separation device. For example, separation methods conventionally used in the oilfield industry can include gravity separation, centrifugation, and hydrocyclone separation. Conventional methods are used to separate large quantities (i.e. for production purposes) and have several drawbacks. One drawback of conventional separation techniques is the time it takes to perform them. Conventional separation techniques often take a long time, depending on the particular composition of the fluid. For example, a fine emulsion may take months to separate by gravity, although a simple mixture may take only a few minutes. Another drawback of conventional separation techniques is poor separation performance. Conventional separation techniques usually do not perform a complete separation. There are almost always traces of contaminants in the sample fluid of interest.

In addition, in most oilfield applications, analyses of formation fluids of interest are typically performed at the surface adjacent to the well or in a remote laboratory environment. However, bringing sample fluids to the surface, transporting them to a laboratory, and separating the phase mixtures is time consuming, cost inefficient and provides only post-factum information. Moreover, fluid samples collected downhole can undergo various reversible and irreversible phase transitions between the point of collection and the point of laboratory analysis as pressure and temperature conditions change.

Recently, biologists and analytical chemists have started to perform analysis of various fluids in laboratories on a micro-scale. The analysis of minute fluid amounts is accomplished with various microfluidic and/or MEM (Micro Electro-Mechanical) systems. Microfluidic systems or devices are typically comprised of fluidic channels with lateral dimensions ranging from tens to hundreds of micrometers and are designed to operate with extremely small volumetric flow rates. However, similar to analysis on a macro-scale, at the micro-scale it is equally necessary to separate the fluid of interest from other fluids in order to perform an effective analysis. Prior to a co-pending patent application Ser. No. 10/885,471 filed Jul. 6, 2004 and entitled "Microfluidic System for Chemical Analysis," which is hereby incorporated in its entirety by this reference and is assigned to the same assignee of this application, along with another co-pending patent application Ser. No. 10/935,858 filed Sep. 8, 2004 as and entitled "Microfluidic Separator," which is hereby incorporated in its entirety by this reference and is assigned to the same assignee of this application, microfluidic devices for oilfield applications have only been suitable for use in laboratory environments.

Accordingly, there is a need for a microfluidic separator capable of separating emulsions, liquid-liquid and liquid-gas mixtures in any environment while minimizing fouling of the membrane, fouling can include a filter cake build-up and/or clogging of membrane pores by particulates or other particulates in the fluid, which can include uphole and downhole oilfield environments.

SUMMARY OF THE INVENTION

According to embodiments of the invention, the invention includes addressing the above-described deficiencies and others. Specifically, the present invention provides methods and apparatus for separating and/or analyzing fluids of interest while minimizing fouling of the membrane. According to principles of the present invention, fluid analysis is accomplished with microfluidic devices and methods and may be reported in real-time or near real-time from a subterranean environment.

According to embodiments of the invention, the invention includes a fluid separation method for performing fluid analysis. The fluid separation method includes providing a structure with a fluid analyzer and a power supply. Using a substrate for receiving a fluid flow stream of a multiphase mixture through a fluid sample inlet, wherein the substrate interconnects with the structure. Providing a membrane disposed across the fluid sample inlet for separating a fluid of interest from the multiphase mixture, wherein the fluid flow stream of the multiphase mixture has a shear rate that prevents a fouling of the membrane. Finally, the fluid separation method includes the substrate having fabricated channels, such that the fabricated channels are arranged substantially tangent to the fluid stream downstream of the porous membrane.

According to aspects of the invention, the method can include the fluid flow stream that can be positioned within at least one channel of the substrate such that the fouling is minimized by one of a size of the at least one channel, at least one corrugated surface of the at least one channel, a specific shear rate or some combination thereof. The shear rate can be determined by a flow rate of the fluid flow stream in the at least one channel along with a size of the at least one channel. The at least one channel plate can have a geometry shape approximate to a serpentine pattern, whereby increasing an average shear rate reduces the fouling on the membrane. It is noted, the fluid flow stream can be in communication with at least one filtration stage prior to the fluid flow stream entering into contact with the membrane, such that the at least one filtration stage includes a first filter that removes at least some particulates from the fluid flow stream. It is possible the at least one filtration stage can include a second filtration stage, wherein a second filter uses capillary forces to extract one of an aqueous phase or a hydrocarbon phase.

According to aspects of the invention, the method can include the structure that can be from the group consisting of one of a wireline conveyed downhole tool, a drill pipe conveyed downhole tool, an oilfield related downhole tool or an other related downhole conveyance device. The method can further comprise of maintaining a pressure difference across the membrane below a capillary break-through pressure of a nonwetting component of the multiphase mixture. The method can further comprise of inserting the membrane and the structure into a subterranean oilfield environment. For example, the separating can comprise part of a measurement while drilling operation, a wireline operation or a permanent production logging operation. Further, the separating can be done by a surface device for mud sample analysis. The separating can be done inside a fluid sample bottle. It is possible the membrane can comprise of one of a water-repellant, oil-permeable membrane, an oil-repellent, water-permeable membrane, an oil-and-water-repellent or a gas-permeable membrane. Further still, the separating can comprise of flowing the liquid of interest from the multiphase mixture through the membrane at a flow rate at least one-to-two orders of magnitude lower than a flow rate of the multiphase mixture passing by the membrane. It is noted the separating can comprise of passing the liquid of interest from the multiphase mixture through the membrane and preventing the membrane from fouling without back-flushing.

According to aspects of the invention, the method can further comprise of maintaining substantially equal pressure drop across an entire area of the membrane, wherein maintaining substantially equal pressure can comprise supporting the membrane with the fabricated channels. The fabricated channels can be a microseive comprised of an H-fractal fluid channel configuration. The separating can comprise part of a measurement while drilling operation, a wireline operation, a permanent production logging operation, a mud logging operation, or a laboratory analysis. The fluid analyzer can include measuring one or more properties of the fluid such as rheological properties. The fluid analyzer can include measuring one or more properties of the fluid such as fluid composition. The fluid analyzer can include measuring one of a surface tension of the fluid, a standard pressure volume temperature (PVT) analysis or other thermodynamic phase measurements. The fluid analyzer can include measuring one or more properties of the fluid such as a pressure, a density, a viscosity, a temperature or some combination thereof.

According to embodiments of the invention, the invention includes an apparatus. The apparatus includes a microfluidic device comprising a porous membrane for separating a multiphase mixture in a fluid flow stream within a structure wherein a pressure difference across the porous membrane is maintained below a capillary break-through pressure of a nonwetting fluid phase present in the multiphase mixture. Wherein the porous membrane is arranged substantially tangent to an intended fluid flow direction of the multiphase mixture present in the fluid flow stream such that the fluid flow stream is directed by at least one channel plate positioned approximate to the membrane and disposed across a fluid sample inlet to the microfluidic device. Finally, a microsieve is structured and arranged adjacent to and downstream of the membrane and includes a capillary fluid separator having microfabricated channels arranged substantially tangent to the fluid stream downstream of the porous membrane.

According to aspects of the invention, the invention can include the fluid flow stream of the multiphase mixture that can be positioned within at least one channel of the microfluidic device, such that the fluid flow stream has a shear rate, whereby a specific average shear rate of the shear rate prevents a fouling on the membrane such that the fouling includes a filter cake build up, a clogging of a pore of the membrane or both. The fouling can be minimized by a determined shear rate, a size of the at least one channel, at least one corrugated surface of the at least one channel or some combination thereof. The determined shear rate can be calculated by a flow rate of the fluid flow stream in the at least one channel along with a size of the at least one channel. The at least one channel can include at least one non-linear surface, at least one corrugated surface, at least two linear surfaces separated by a non-linear surface or some combination thereof. The at least one channel can be shaped as one of a uniform shape, a non-uniform shape, a geometric shape or a wave-type shape. The at least one channel plate can have a geometry shape approximate to a serpentine pattern, whereby increasing the average shear rate so as to reduce the fouling on the membrane.

According to aspects of the invention, the invention can include the fluid flow stream that can be in communication with at least one filtration stage prior to the fluid flow stream entering into contact with the membrane, such that the at least one filtration stage includes a first filter that removes at least some particulates from the fluid flow stream. The at least one filtration stage can include a second filtration stage, wherein the second filtration stage has a second filter that uses capillary forces to extract one of an aqueous phase or a hydrocarbon phase. The structure can be from the group consisting of one of a wireline conveyed downhole tool, a drill pipe conveyed downhole tool, an oilfield related downhole tool or an other related downhole conveyance device. The structure can be a submersible housing surrounding the microfluidic device. One or more mesh device can be positioned approximate the at least one channel plate. The structure is an uphole device used above ground. The microfluidic device can comprise of a sample manipulation/analysis module or a chip. The sample manipulation/analysis module or the chip can include measuring one or more properties of the fluid such as rheological properties. The fluid analyzer can include measuring one or more properties of the fluid such as fluid composition. The fluid analyzer can include measuring one of: a surface tension of the fluid; a standard pressure volume temperature (PVT) analysis; or other thermodynamic phase measurements.

According to embodiments of the invention, the invention includes an apparatus. The apparatus includes a housing having a fluid flow stream such that the housing is positioned in a downhole oilfield tool. The apparatus includes a microfluidic device positioned in the housing comprising a porous membrane for separating a multiphase mixture in the fluid flow stream wherein a pressure difference across the porous membrane is maintained below a capillary break-through pressure of a nonwetting fluid phase present in the multiphase mixture and the fluid flow stream is directed by at least one channel plate positioned approximate to the porous membrane. The porous membrane can be arranged substantially tangent to an intended fluid flow direction of the multiphase mixture present in the fluid flow stream. Finally, a microsieve structured and arranged adjacent to and downstream of the porous membrane and includes a capillary fluid separator having microfabricated channels arranged substantially tangent to the fluid flow stream downstream of the porous membrane.

The fluid separation method can include inserting the membrane and the microfluidic device into a subterranean oilfield environment and the separating comprises separating the multiphase mixture in a wellbore. The separating can further be part of a measurement while drilling operation, a wireline operation, or a permanent production logging operation, such that the separating can be done by a surface device for mud sample analysis. It is possible the separating can be done inside a fluid sample bottle and that the separating can further include separating one liquid of the multiphase mixture from another liquid. It is noted that the separating can include creating a pressure differential across the membrane in the microfluidic device as well as separating a gas and/or liquid from the multiphase mixture. It is possible that method includes separating a first liquid in a multiphase mixture from a second liquid in the multiphase mixture with one of a membrane or a plurality of microfabricated pores in a microfluidic device. Further, the separating may include part of a measurement while drilling operation, a wireline operation, a permanent production logging operation, mud logging operation, or laboratory analysis.

According to an embodiment of the invention, the invention can include the method of testing a subterranean fluid in situ, comprises: a) separating a fluid of interest from another fluid downhole in a microfluidic device; b) passing the separated fluid of interest into a microfluidic analyzer; and c) analyzing the fluid of interest and reporting the analysis uphole in near real-time. Further, analyzing can comprise of continuously passing a new supply of the separated fluid of interest into the microfluidic analyzer. It is noted that the analyzing can comprise of passing a new supply of the separated liquid of interest at different depths in a wellbore during a drilling or wireline logging operation.

According to an embodiment of the invention, the invention can include the method of separating a multi-phase mixture having at least one fluid of interest and at least one fluid not of interest. Sending the multi-phase mixture through a microfluidic channel in contact with a membrane wet by at least one fluid not of interest. Permeating the one or more fluids not of interest through the membrane, and leaving a stream of at least one fluid of interest to flow to an outlet of the microfluidic channel.

According to an embodiment of the invention, the invention can include the method of separating a multi-phase mixture of two or more immiscible fluids. Further, sending the multi-phase mixture through a first microfluidic channel in contact with a membrane wet by a first of the two or more immiscible fluids. Then, passing the first fluid through the membrane, collecting the first fluid in a second microfluidic channel, and directing the first fluid to an outlet of the second microfluidic channel. Finally, the method includes leaving a second of the two or more immiscible fluids to flow to an outlet of the first microfluidic channel. It is possible, the method can further comprise analyzing the first and second fluids.

According to an embodiment of the invention, the invention can include a microfluidic device comprising a porous membrane for separating a multiphase mixture. The microfluidic device may be surrounded by a submersible housing. The membrane may be a hydrophobic membrane, an oleophobic membrane, a hydrophobic/oleophobic gas permeable membrane, or some other separation membrane. The membrane may comprise PTFE, polyethylene, polypropylene, nylon, or other materials. The apparatus may include a microsieve adjacent to and downstream of the membrane. The porous membrane may be mechanically connected or adhesively connected to the microsieve. Various chemical modifications may be performed on the porous membrane in order to increase its adhesive properties. The apparatus may include a downhole oilfield tool having a fluid flow stream, such that the microfluidic device is disposed in the fluid flow stream and the porous membrane is arranged substantially tangent to a flow direction of the fluid flow stream. The microfluidic device may have a sample manipulation/analysis module or chip. The microfluidic device may also include a capillary gas separator downstream of the porous membrane. The capillary gas separator may comprise microfabricated channels arranged substantially tangent to a fluid stream downstream of the porous membrane. The microfabricated channels may comprise pores of approximately 10 microns or less. The microfluidic device may include a secondary fluid outlet channel tangentially downstream of the capillary gas separator, and an oil outlet downstream of the capillary gas separator.

Another embodiment of the present invention comprises a microfluidic system for performing fluid analysis comprising a submersible housing having a fluid analyzer and a power supply to provide power to said system, a substrata for receiving a multiphase mixture through a fluid sample inlet, wherein the substrate interconnects with the housing, and a membrane disposed across the fluid sample inlet for separating a fluid of interest from the multiphase mixture. It is also possible that the substrate could be a channel plate which can be defined as a substrate having at least one channel.

Another aspect of the invention provides a method of separating a multi-phase mixture of two or more immiscible fluids, comprising: sending the multi-phase mixture through a first microfluidic channel in contact with a membrane wet by a first of the two or more immiscible fluids, passing the first fluid through the membrane, collecting the first fluid in a second microfluidic channel, directing the first fluid to an outlet of the second microfluidic channel, and leaving a second of the two or more immiscible fluids to flow to an outlet of the first microfluidic channel. The method may further include analyzing the first and second fluids.

Additional advantages and novel features of the invention are set forth in the description which follows or may be learned by those skilled in the art through reading these materials or practicing the invention.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

According to embodiments of the invention, the invention includes a fluid separation method for performing fluid analysis. The fluid separation method includes providing a structure with a fluid analyzer and a power supply. Using a substrate for receiving a fluid flow stream of a multiphase mixture through a fluid sample inlet, wherein the substrate interconnects with the structure. Providing a membrane disposed across the fluid sample inlet for separating a fluid of interest from the multiphase mixture, wherein the fluid flow stream of the multiphase mixture has a shear rate that prevents a fouling of the membrane. Finally, the fluid separation method includes the substrate having fabricated channels, such that the fabricated channels are arranged substantially tangent to the fluid stream downstream of the porous membrane.

According to embodiments of the invention, the invention includes methods and apparatus for separating multiphase mixtures including liquid-gas mixtures, liquid-liquid mixtures, and emulsions, especially in microfluidic devices while minimizing fouling of the membrane. As mentioned in the background, in many applications, including oil well evaluation and aquifer management, fluid samples must be separated and analyzed. The principles described herein facilitate separation of liquid-liquid mixtures and liquid-gas mixtures. The separation according to the present invention may take place in a downhole environment during wireline operations, while drilling (Logging While Drilling (LWD)/Measurements While Drilling (MWD)), during permanent production logging, and is not limited to laboratory conditions. However, the principles described herein may be used at a surface or laboratory location as well. Application of the principles of the present invention may be used, for example, to provide continuous real-time or near real-time data concerning formation fluid in a subterranean formation.

As used throughout the specification and claims, the terms "microfluidic system" or "microfluidic device" mean a network of one or more channels with dimensions of tens to hundreds of micrometers that may have one or more components including, but not limited to: pumps, valves, mixers, integrated optical fibers, and other components integrated on a chip for the purpose of manipulating and/or analyzing minute amounts of fluid. The term "tangentially downstream" refers to a fluid stream, a portion of which is flowing by, rather than through, a stated component. "To foul" means to become clogged, obstructed, or blocked. "Fluid" means a continuous, amorphous substance whose molecules move freely past one another and that has the tendency to assume the shape of its container, including both liquids and gases. In the context of membranes, "hydrophobic" is the property of a material of not being wet by water (water impermeable). "Hydrophilic" is the property of being wet by water (water permeable). "Oleophobic" means not wet by oil (oil impermeable) and "oleophilic" means wet by oil (oil permeable). "Microsieve" refers to a network of microchannels in contact with a membrane used for collecting a fluid of interest permeating through a membrane. The words "including" and "having," as used in the specification, including the claims, have the same meaning as the word "comprising." The term "fouling" can include filter cake build up, a clogging of the pores of the membrane or the like. Further, filter cake build-up can also consist of oilfield emulsions or "emulsions", which have been found to particularly impede flow of liquid through the membrane. Still referring to the term emulsions, the crossflow on the membrane is particularly advantageous here as it continually sweeps the membrane surface of the undesired phase, which may by emulsified water droplets in oil. Further referring to the term emulsions, if these water droplets are not swept off of the membrane they eventually build up into a gel-like filter-cake which completely prevents the desired fluid from going through the membrane.

The principles of the present invention may be extended to any application wherein multi-phase separation may be useful. For example, the principles of the present invention may be applied to biological samples, chemical samples, or any other microfluidic samples and are not limited to oilfield applications.

Small-scale sensors are currently being considered in the oil industry, in particular for performing measurements in downhole environments. Miniaturized sensors capable of monitoring pressure, density, viscosity, and temperature are also being considered in the oil industry. There are several reasons for considering miniaturization, for example reduced fabrication costs (such sensors can be batch-produced), smaller size (a sensitive parameter given the limited space available in the downhole environment is needed), and lower power consumption is also needed. In addition, using miniaturized sensors such as a fluid analyzer in accordance with principles of the present invention, can provide measurements that typically involving large lab equipment may instead be performed downhole in the natural environment. For example, the fluid analyzer can include measuring one or more properties of the fluid such as rheological properties such as, by non-limiting example, density and viscosity. Further, the fluid analyzer can include measuring one or more properties of the fluid such as fluid composition. The fluid analyzer can include measuring one of a surface tension of the fluid, a standard pressure volume temperature (PVT) analysis or other thermodynamic phase measurements. It is also possible the fluid analyzer can include measuring one or more properties of the fluid such as a pressure, a density, a viscosity, a temperature or some combination thereof.

Among the properties that could not be fully characterized downhole prior to the present invention is the chemical composition of the various fluids extracted from the formation. As mentioned in the background, one obstacle to downhole chemical analysis is efficiently separating phases (e.g. oil, water, gas, particulates, contamination from drilling muds, etc.). Filtering usually fails due to filter fouling, e.g., fouling includes cake build-up, clogging of the pores of the membrane or the like, and gravitational separation based on density mismatch is extremely slow. Accelerated separation methods such as centrifugation and hydrocyclone separation are difficult to implement and impractical in a downhole environment.

Figure 1:
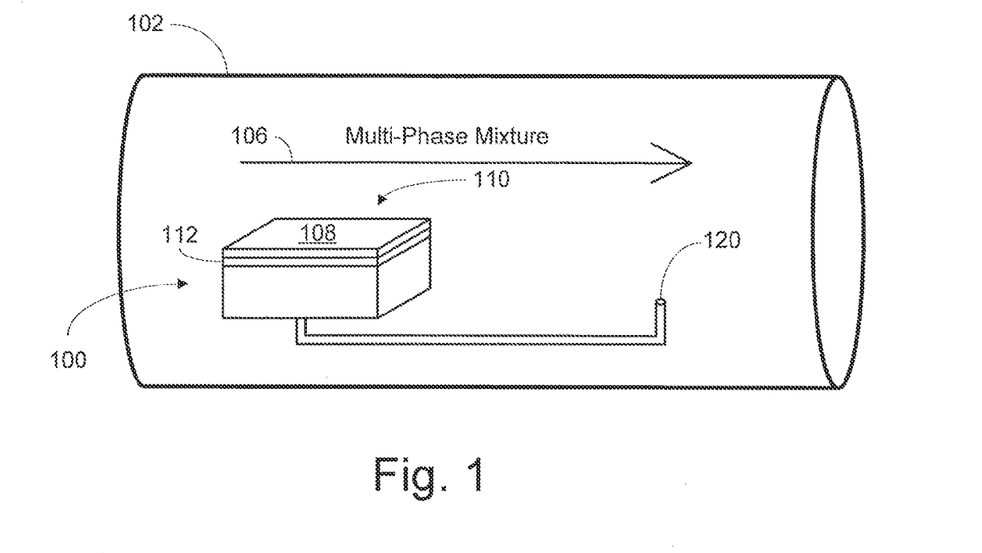
FIG. 1 is a schematic diagram of a sample tool with a microfluidic device and a separator according to one embodiment of the present invention.

Therefore, according to the present invention, a microfluidic device or system 100 shown in FIG. 1 includes a multi-phase separator that may be used in downhole environments without the tendency to foul. The description that follows includes a discussion of apparatus according to principles of the present invention, followed by a description of microfluidic and microanalysis systems in general, and an explanation of methods of practicing the invention.

Microfluidic Separator

FIG. 1 illustrates a sampling tool 102 in fluid communication with formation fluid mixtures. An intended flow direction of fluids with respect to the sampling or drilling tool 102 is represented by an arrow 106.

Referring to FIG. 1 and according to principles of the present invention, the multi-phase separator of the microfluidic device 100 shown in FIG. 1 relies on differences in wetting behavior between various fluids on certain materials and microstructures in order to perform separation of the multi-phase fluids. Certain materials and microstructures contain pores or capillaries which are wetted by certain fluids but not by others. For example, referring to FIG. 2, a pore 107 is wet by Fluid A but not by Fluid B. Therefore, Fluid A flows freely through the pore 107 whereas the nonwetting Fluid B forms a meniscus 109 which prevents Fluid B from entering the pore 107. If pressure applied across the pore 107 becomes larger than a certain breakthrough pressure, Fluid B will enter the pore 107. However, if the pressure of Fluid B is maintained below the breakthrough pressure, only Fluid A will flow through the pore.

Referring to FIG. 1, the magnitude of the breakthrough pressure of a fluid depends on the surface properties (such as surface energy) of the material that incorporates the pores, the dimensions of the pore (such as diameter), and the surface tension of the two immiscible fluids and of their interface (e.g. Fluids A and B).

Still referring to FIG. 1, the multi-phase separator comprises microfabricated channels or a porous membrane 108 disposed at or across a fluid sample inlet 110. The porous membrane 108 preferably has high porosity and submicron pore size. Therefore, the porous membrane 108 provides both capillary separation of a fluid of interest (such as oil) from a secondary fluid or liquid (such as water), and particulate filtering. According to the embodiment of FIG. 1, the membrane 108 may be made of hydrophobic, oleophilic material; hydrophilic, oleophobic material, or a material that is gas permeable and both hydrophobic and oleophobic. Other materials may also be used. The membrane 108 is capable of liquid-liquid separation and/or gas-liquid separation without fouling. The membrane 108 is preferably made of a suitable chemically and thermally resistant material, such as PTFE (polytetrafluroethylene, known under the brand name of Teflon®) for Goretex® or Porotex® membranes, polyethylene/polypropylene for Celgard® membranes, nylon, or other material.

As shown in FIG. 1, the membrane 108 is placed across the inlet 110 adjacent to a microsieve 112. Nevertheless, the membrane 108 may be located anywhere between the inlet 110 and an outlet 120. The microsieve 112 is optional. However, the microsieve 112 provides a support or backing to the membrane 108 and creates a uniform distribution of pressure over the entire area of the membrane 108. The microsieve 112 is preferably integrated with the microfluidic system 100 and may comprise a wire mesh or closely perforated plate. The membrane 108 may be mechanically connected to the microsieve 112. The mechanical connection between the membrane 108 and the microsieve 112 may be achieved according to some embodiments by pressing the membrane 108 with an o-ring or other fastener, or it may be adhesively attached. Chemical modifications may be performed on the membrane material in order to improve its adhesive properties. The membrane 108 is preferably in direct contact with the microsieve 112, minimizing dead-volume issues which can become problematic in low flow rate regimes.

As shown in FIG. 1, the assembly comprising the membrane 108 and microsieve 112 is preferably arranged substantially tangent to or parallel with the intended flow direction 106 of fluids flowing through or along the sampling tool 102. Furthermore, the flow rate through the membrane 108 is extremely low, on the order of several microliters per minute, which corresponds to a very low pressure drop across the membrane 108. The pressure drop across the membrane 108 is preferably maintained well below the pressure necessary for capillary break-through of the nonwetting fluid. The configuration of the membrane 108 disposed substantially in a tangent or cross-flow direction with respect to the fluid advantageously results in self-cleaning of the membrane 108. The flow rate across or passing by the membrane 108 is at least one-to-two, and preferably several, orders of magnitude larger than the flow rate through the membrane 108. Therefore, cake build-up and fouling problems are prevented, eliminating the need to backflush.

Figure 2:
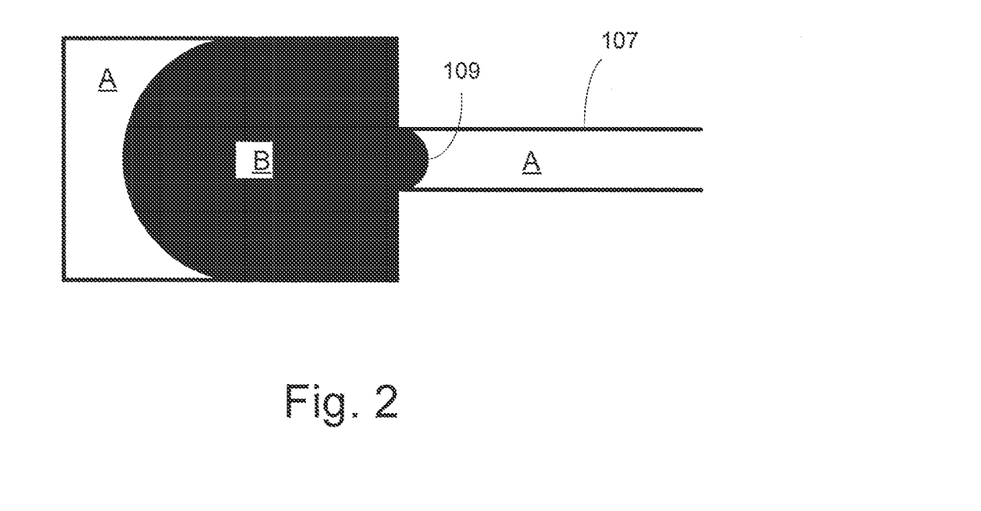
FIG. 2 is a representative diagram illustrating wetting properties of two different fluids with respect to a pore.
Figure 3:
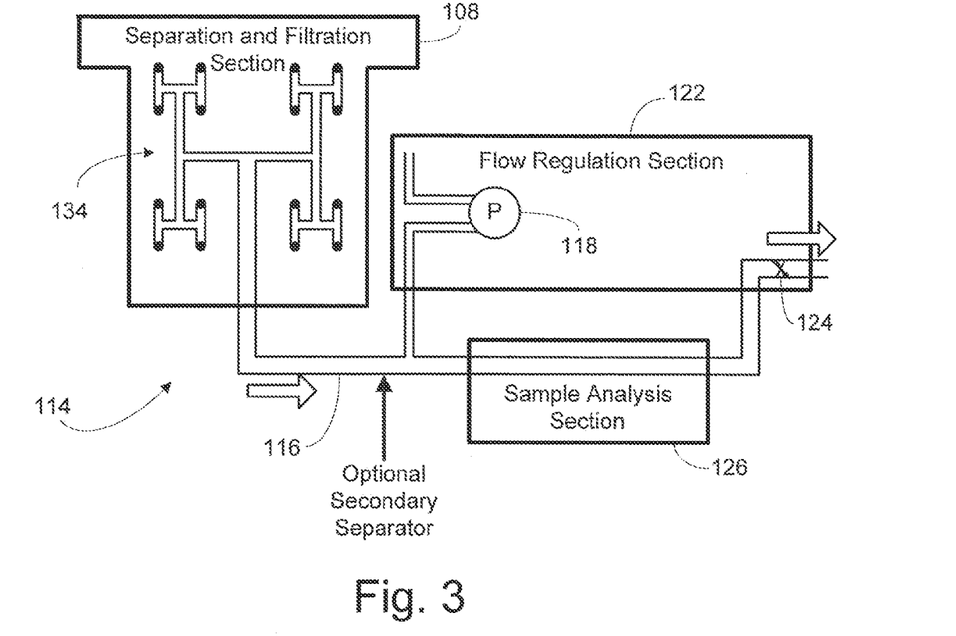
FIG. 3 is a block diagram illustrating details of the microfluidic device and separator of FIG. 1 according to one embodiment of the present invention.

Referring to FIGS. 1-3, the membrane 108 and microsieve 112 assembly may be connected to or integral with the microfluidic system 100, which, according to the schematic embodiment of FIG. 3, is a microfluidic sample manipulation/analysis sensor chip 114. As shown in FIG. 3, the microfluidic sensor chip 114 is configured to manipulate and analyze microscopic (few microliters and smaller) amounts of fluid. Suction pressure to assure flow through the membrane 108, microsieve 112 (FIG. 1), and the channels 116 disposed in the chip 114 may be generated either actively or statically. According to FIG. 3, a pressure gauge 118 may monitor the pressure drop across the membrane 108 of the chip 114. One or several valves 124, possibly in conjunction with a micropump, may be used in order to maintain the pressure drop below the breakthrough pressure of the nonwetting phase, as part of a flow regulation system 122. However, according to other embodiments, an inherent flow-generated pressure drop inside a wellbore or oil pipe between the inlet 110 (FIG. 1) and an outlet 120 (FIG. 1) of the microfluidic sensor chip 114 may provide the suction pressure.

Figure 4:
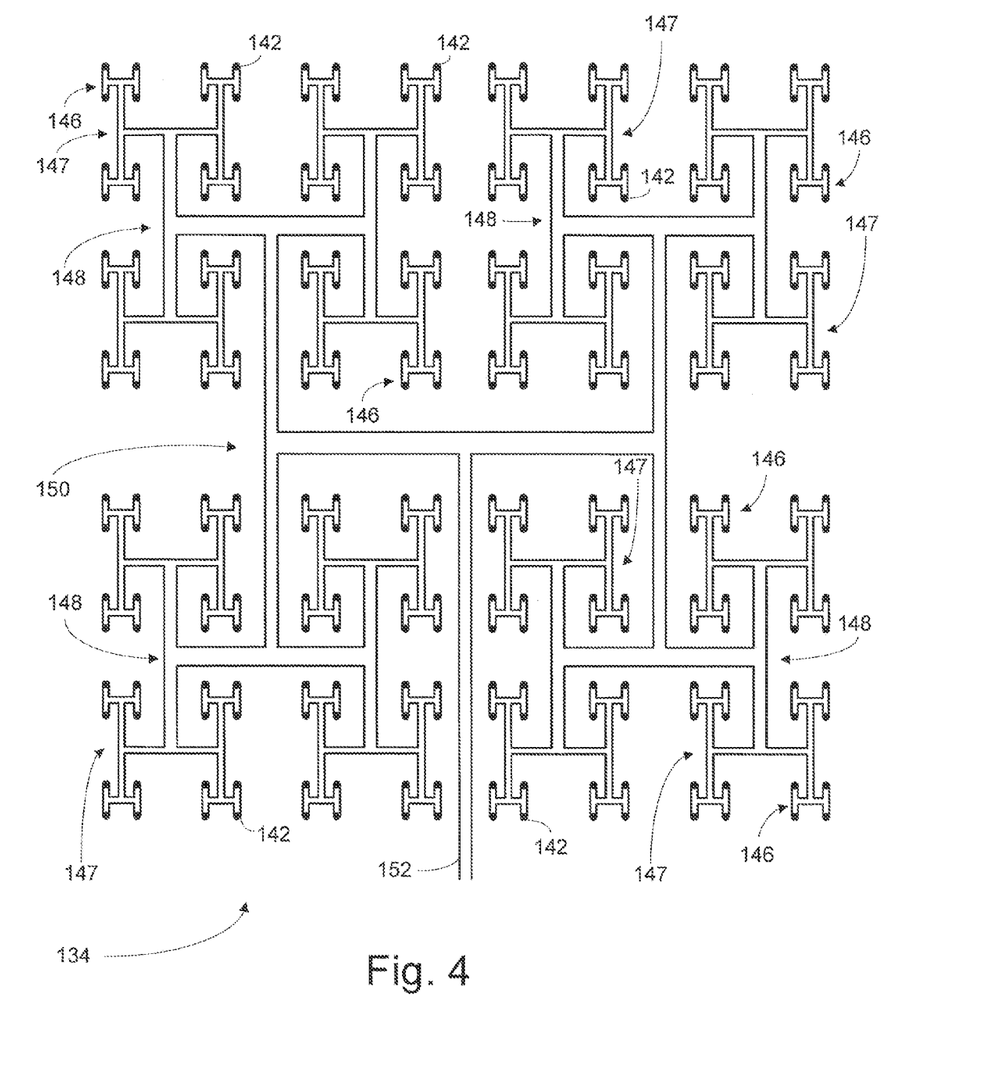
FIG. 4 is an illustration of an H-fractional microfluidic channel arrangement according to one embodiment of the present invention.

Referring to FIGS. 3-4, as a fluid of interest such as liquid oil passes through the membrane 108, it enters an interconnected arrangement of collection channels. According to the embodiment of FIG. 3, the collection channels comprise an H-fractal configuration 134. FIG. 4 illustrates details of the H-fractal configuration. As shown in FIG. 4, the collection channels comprise a plurality of nodes 142, four nodes for each of a plurality of first H's 146. Fluid may enter the configuration 134 at each of the nodes 142. Each of the first H's 146 is in fluid communication with adjacent first H's 146 to form a second set of H's 147. According to the embodiment shown, a set of four adjacent first H's 146 cooperate to form a second H 147. Likewise, each of the plurality of second H's 147 is in fluid communication with one another to create a third plurality of H's 148. According to the embodiment shown, four of the second plurality of H's 147 cooperate to form a third H 148. Each of the third plurality of H's 148 is in fluid communication with one another to create a fourth H 150. The pattern shown in FIG. 4 may obviously be expanded or contracted as desired. The fourth H 150 is in fluid communication with a fluid outlet channel 152, which feeds into the channel 116 shown in FIG. 3. One advantage of the H-fractal configuration is an equidistant fluid path length between each node 142 and the fluid outlet channel 152. Therefore, regardless of what node 142 a volume of fluid enters, all volumes of fluid entering the different nodes 142 at the approximate same time will also reach the fluid outlet channel 152 at substantially the same time, improving the response time of the system. In addition, this configuration may also improve the uniformity of fluid sampling across the filter.

Still referring to FIG. 3, the fluid outlet channel 152 may feed a sample analysis section 126 of the chip 114 shown in FIG. 3. The functions of the sample analysis section 126 are discussed in more detail below. However, there may also be an intermediate or secondary separator through which sample fluid flows before entering the sample analysis section 126 as discussed below.

According to some embodiments, the membrane 108 separates fluids such as liquids of interest (e.g. oil) from other fluids (which may be liquids such as water). In addition, the membrane 108 is capable of separating liquids of interest from gases. However, it is possible that some gas may be dissolved in the liquid of interest as it passes through the membrane 108. Bubbles may form from the dissolved gas due, for example, to the differential pressure across the membrane 108. Therefore, according to some embodiments, a second separator, which is preferably a liquid-gas separator, may be arranged downstream of the membrane 108.

Figure 5:
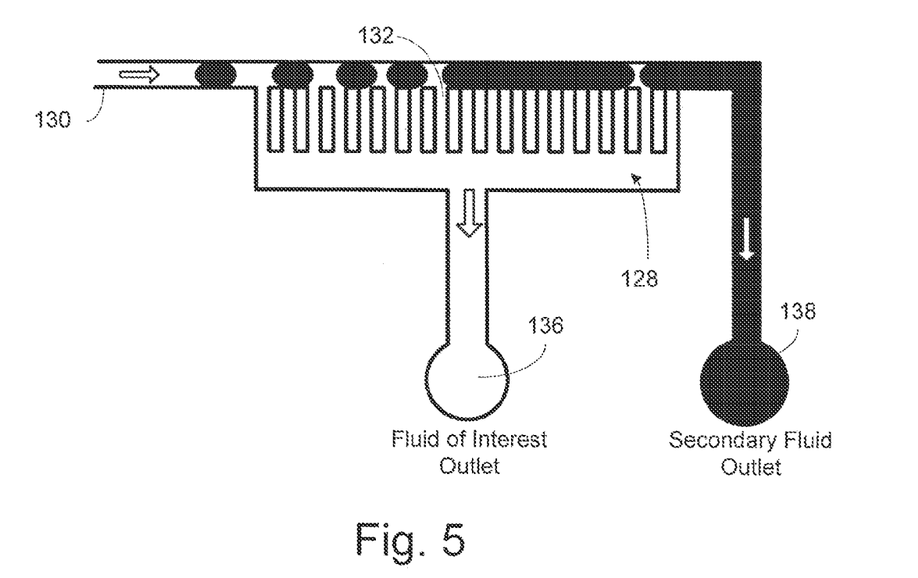
FIG. 5 is a schematic diagram illustrating a second separator that may be combined with the separator shown in FIGS. 1-2 according to one embodiment of the present invention.

According to the embodiment of FIG. 5, the second separator is a capillary gas separator comprising a plurality of microfabricated pores such as microfabricated filter 128. The microfabricated filter 128 is optional, but may, however, replace the membrane 108 and function as a primary fluid separator. As shown in FIG. 5, the microfabricated filter 128 is arranged substantially tangent to a fluid stream flowing through a channel 130 downstream of the porous membrane 108 (FIG. 1). Microfluidic channels such as the channel 130 that transports emulsions or other fluids may be tens to hundreds of microns wide and deep. On the other hand, the microfabricated filter 128 preferably comprises pores such as hydrophobic, oleophilic pores; or hydrophilic, oleophobic pores 132 on the order of approximately 10 microns or less. Only the fluid of interest (that wets the pore material) passes through the pores 132, while other fluids (such as water in the case of hydrophobic pores) tend to flow tangentially past the filter 128.

Referring to FIGS. 3 and 5, the fluid of interest passes through the microfabricated filter 128 as a single phase to the sample analysis section 126 (FIG. 3), where it is manipulated and/or analyzed and discharged through an outlet 136. The secondary fluid and any separated phases pass by the microfabricated filter 128 and eventually out of the microfluidic device 100 through a secondary fluid outlet 138.

Still referring to FIGS. 3 and 5, the single phase samples of the fluid of interest (which may be, for example, oil, water, gas, biological fluids, etc.) may undergo one or more of several possible analyses in the sample analysis section 126 (FIG. 3). For example, the sample analysis section 126 (FIG. 3) may perform functions including, but not limited to: gas chromatography, mass spectroscopy, titration, visible/infrared absorption spectroscopy, fluorescence detection, resistivity measurements, and physical measurements such as pressure, density, viscosity, and temperature. As discussed below, these functions can be built into the sample analysis section 126 (FIG. 3) according to conventional methods by those of skill in the art having the benefit of this disclosure.

According to some aspects of the invention, fluid may pass into or through the microfluidic system 100 (FIG. 1) once, at intervals, or even continuously to monitor properties (and contamination) of a phase of interest and provide real-time data uphole. The microfluidic system 100 (FIG. 1) may include components such as those described in co-pending patent application Ser. No. 10/885,471 filed Jul. 6, 2004 to facilitate remote downhole use.

Referring to FIGS. 1-5, microfluidic systems such as the microfluidic system 100 discussed with reference to FIGS. 1-5 can be constructed using standard microfabrication techniques by those of skill in the art having the benefit of this disclosure. For example, the microfluidic system 100 may be fabricated in silicon and bonded to Pyrex® glass or sapphire. Sapphire may be particularly useful due to its good chemical and thermal resistance and excellent optical properties. Having the benefit of this disclosure, the technologies for constructing the microfluidic system 100 are well established and available from numerous commercial and university foundries. In addition, the microfluidic system 100 of the present invention may be constructed using soft lithography (micromolding of an appropriate elastomer, typically silicone-based), using micromolding of various plastic materials or curing certain resins inside pre-made molds.

As mentioned above, flow through the microfluidic system 100 may be actively generated by micro-pumps, which are available from several manufacturers including ThinXXS of Zweibrucken, Germany, and Micropump of Vancouver, Wash. Various valve types (integrated or exterior) commercially available can also be employed to regulate flow as discussed above. Mixers (active or passive) may be used to assure proper mixing of the fluids involved in the flow through the microfluidic system 100. Mixers may be helpful, for example, to homogenate an analyte-reagent mixture.

The microscopic fluid samples acquired and separated according to the principles described herein may be analyzed as indicated above. Gaseous phase chromatography is commercially available as a MEM sensor chip from, for example, Agilent. Several types of physical sensors, including those mentioned above for measuring temperature, pressure, coefficient of viscosity, density, etc. can also be included. Chemical analyses can be achieved by titration and/or absorption spectroscopy as light is channeled to the microfluidic chip 114 (FIG. 3) by waveguides or fiber optics, and transmitted light can be collected and analyzed. Fluorescence of various components can also be detected.

Figure 6:
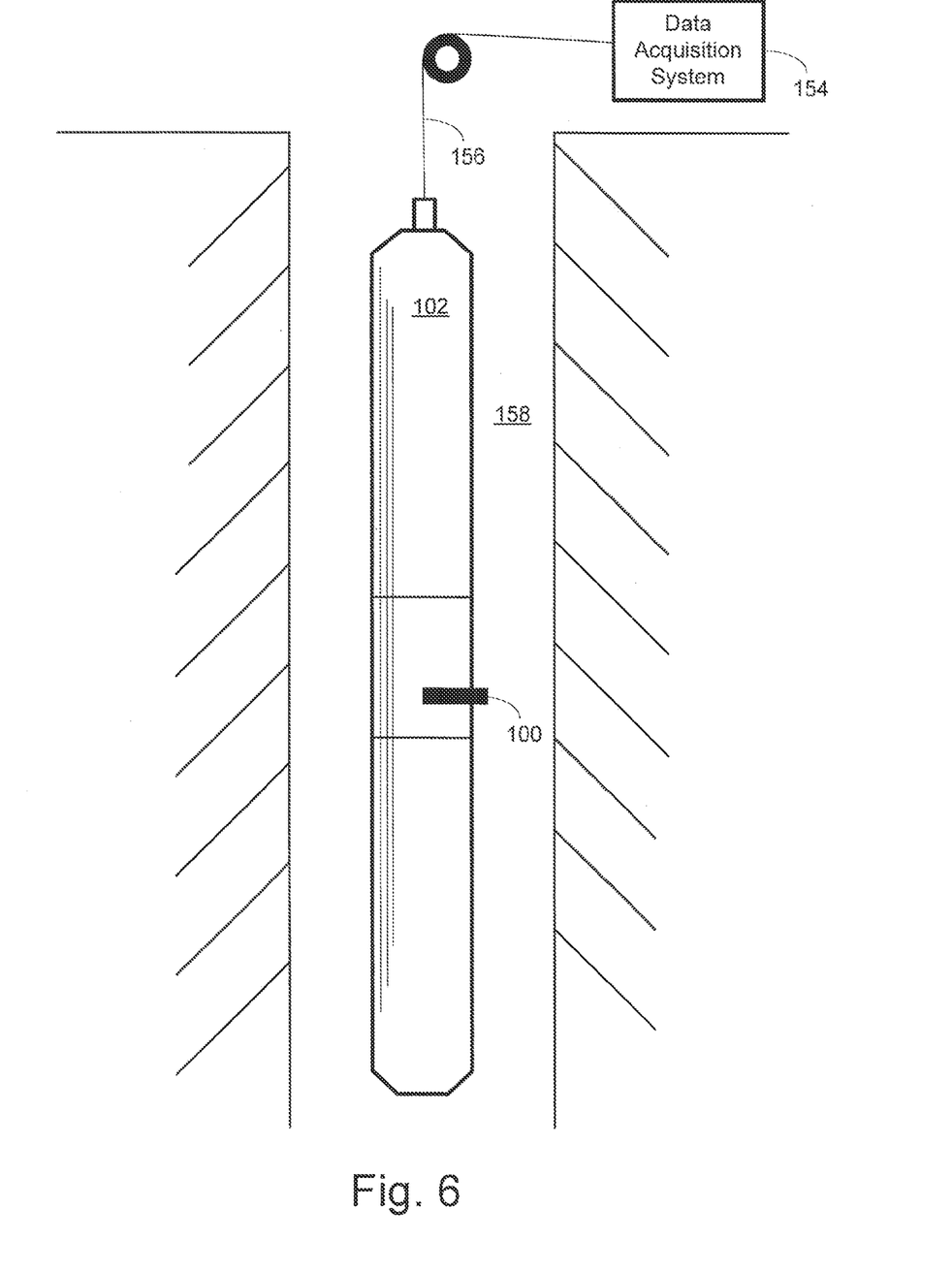
FIG. 6 is an illustration of one application of the present invention, useful for oilfield fluid monitoring and water management.

Referring to FIG. 1-8, and according to principles of the present invention, a component phase of interest such as liquid oil may be efficiently collected and tested remotely in a downhole environment or at the surface. Referring to FIG. 6, the drilling or sampling tool 102 may be lowered downhole and a stream of sample fluid containing a liquid of interest (such as liquid oil) flows across the microfluidic device 100. A separator of the microfluidic device 100 such as the porous membrane 108 (FIG. 1) or the microfabricated filter 128 (FIG. 5) separates the liquid of interest at the inlet 110 (FIG. 1) or elsewhere. The liquid of interest is channeled through the microfluidic device 100, and the liquid of interest may be further separated from gases by a second separator such as the microfabricated filter 128 (FIG. 3), or a secondary membrane embedded within the microfluidic system (e.g. FIGS. 7-8). The liquid of interest passes to a microfluidic analyzer such as the sample analysis section 126 (FIG. 3) of the microfluidic device 100. The sample analysis section 126 (FIG. 3) analyzes the liquid of interest and provides real-time or near real-time data ("near" indicating a small communication lag time) uphole to a data acquisition system 154 or operator via a communication medium 156. Alternatively, sample analysis results may be presented to lab personnel. The flow of sample fluids into the sample analysis section 126 (FIG. 3) may occur once, continuously, or at multiples depths in a wellbore 158. As mentioned above, the principles described herein may be used for surface analysis, wireline operations, production logging, logging/measurement while drilling, or other applications.

Referring to FIG. 6, it will be understood by those of skill in the art having the benefit of this disclosure that the wireline configuration shown in FIG. 6 is exemplary in nature. Other suitable tools and configurations may also incorporate the principles of the present invention. For example, permanent monitoring installations, drilling tools, surface devices (for example to collect and analyze drilling mud samples), sample bottles, biological or chemical laboratory equipment, or other apparatus may include a microfluidic device with a separator according to the present invention.

Figure 7:
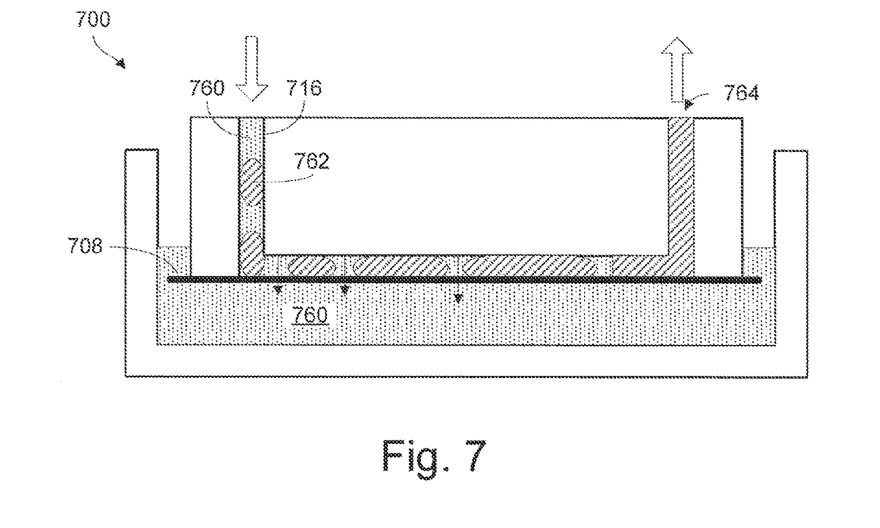
FIG. 7 is a representation of a microfluidic separator and method of separating according to another aspect of the present invention.

Referring to FIG. 7, and according to another embodiment of the invention, there may be a microfluidic separator 700 with a membrane 708 disposed therein. The membrane 708 may be a secondary membrane in addition to the membrane 108 shown in FIG. 1. The microfluidic separator 700 includes a micro channel 716 through which a multi-phase mixture is introduced. The micro channel 716 is fabricated on or in contact with the membrane 708. The multi-phase mixture includes at least two immiscible fluids, shown in FIG. 7 as a first fluid 760 and a second fluid 762 wherein channels for the first fluid 760 and the second fluid 762 are formed by a substrate 703. It is also possible that the substrate 703 could be a channel plate 703 which can be defined as a substrate having at least one channel. The first fluid 760 is a membrane-wetting fluid that permeates through the membrane 708, where it is discarded. The second fluid 762 will not wet the membrane 708. Therefore, as the first liquid 760 permeates the membrane 708, it is eliminated, leaving only the pure nonwetting second fluid 762 being collected at an outlet 764 of the micro channel 716. The second fluid 762 may then be analyzed.

Figure 8:
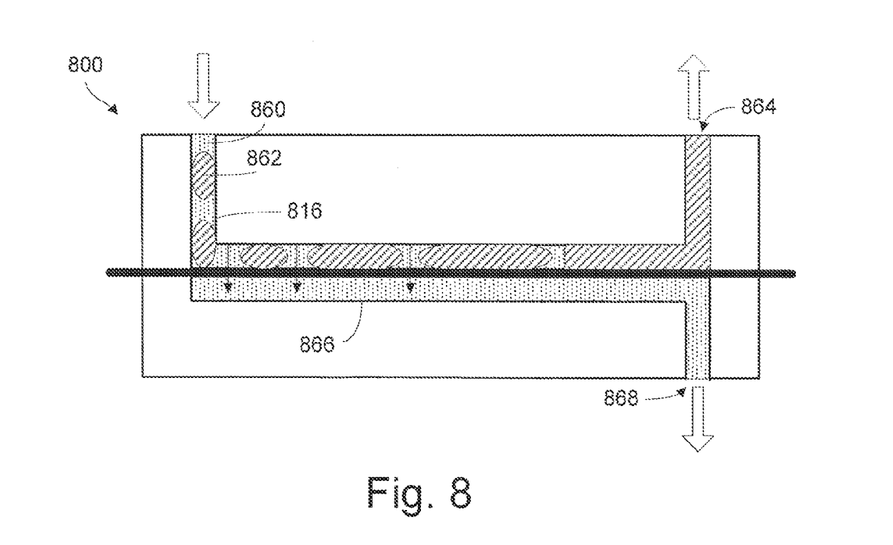
FIG. 8 is a representation of another microfluidic separator and method of separating that may enable analysis of multiple fluids of interest according to another aspect of the present invention.

FIG. 8 is another embodiment similar to the embodiment of FIG. 7. The embodiment of FIG. 8 is also microfluidic separator 800 with a membrane 808 disposed therein. The membrane 808 may be a secondary membrane. The microfluidic separator 800 includes a first micro channel 816 through which a multi-phase mixture is introduced. The first micro channel 816 is fabricated on or in contact with the membrane 808. The multi-phase mixture includes at least two immiscible fluids, shown in FIG. 8 as a first fluid 860 and a second fluid 862. The first fluid 860 is a membrane-wetting fluid that permeates through the membrane 808, where a pure sample thereof is collected by a second micro channel 866 that is in contact with an opposite side of the membrane 808. The first fluid 860 may exit the second micro channel 866 through an outlet 868 and be analyzed. The second fluid 862 is nonwetting to the membrane 808 and therefore a pure volume thereof remains in the first micro channel 816 and may exit through an outlet 864 for analysis as well.

Minimizing Fouling

According to embodiments of the invention, the invention can include a method to minimize fouling, e.g., filter cake build-up, on a membrane such as in the microfluidic separator when exposed to unfiltered fluid, such as live oilfield fluids downhole. For downhole fluids it is found that the primary impediment to flow through such a membrane can be the build-up of the filter cake that occurs as fluid is drawn through the membrane leaving behind particulates and/or fines that are larger than the pore size of the membrane, resulting in generally referred to as membrane fouling. According to at least one aspect of the invention, the invention teaches methods of design and operation that minimizes membrane fouling with fluids, such as downhole fluid, and maximizes the total volume of single-phase fluid that can be extracted in a given span of time through the membrane.

According to embodiments of the invention, the invention can relate to the extraction of a single phase and/or multiphase fluid from a portion of a potentially multi-phase and particulate-laden fluid that may consist of membrane fouling molecules. By non-limiting example, there are at least two possible situations wherein the invention may relate; first, an extraction of a hydrocarbon phase from a mixture of hydrocarbons and aqueous phases; secondly, an extraction of an aqueous phase from a mixture of hydrocarbons and aqueous phases. Further, for example, the above mentioned mixtures can be referred to as "multi-phase" fluids. It is noted that depending upon the fluid present (entering the microfluidic separator) and the fluid that it is to be extracted by the membrane, it may be more favorable to use a single-stage approach. Below is a discussion of the single-stage approach, and then later a discussion of the multi-stage approach.

According to the co-pending patent applications referenced above, which is incorporated herein by reference in its entirety, and is assigned to the same assignee of this application, has shown, extraction of a desired phase from a multi-phase mixture can be achieved with a microfluidic separator by use of a suitable membrane. Unfiltered fluid is circulated parallel to the membrane surface and a pressure differential is created such that a small fraction of the fluid is induced to flow through the membrane. The cross-membrane pressure differential is defined as the pressure that induces the fluid to flow parallel to the membrane surface and the transmembrane pressure differential is defined as the pressure that induces the fluid to flow through the membrane. In a similar fashion, the cross-membrane and transmembrane flow rates correspond to the unfiltered fluid flow parallel to the fluid surface and that through the membrane surface respectively. One can say that the membrane in the microfluidic separator wicks off a very small fraction (transmembrane flow) of the fluid flowing across its surface (cross membrane flow). The cross membrane flow rate is usually orders of magnitude greater than the transmembrane flow rate. The magnitude of the transmembrane differential pressure is chosen to induce the desired phase to pass through the membrane at the maximum flow rate practicable while not exceeding the capillary pressure which prevents the undesired phase from passing through the membrane. Unfortunately, such filtration processes typically suffer from membrane fouling that dramatically reduces the transmembrane flow rate. Fouling can either consist of a clogging of membrane pores by particulates or other moieties (particulates) in the fluid or a growth of a filter-cake on the membrane surface. For example, fouling, e.g., filter cake build-up, can impede flow through the membrane, such that the build-up can include a gelacious material as a result from operation of the microfluidic membrane over a period of time. The gel may consists of a mixture of flocculated asphaltenes and resins that did not pass through the membrane but rather deposited on the surface, thereby reducing the permeability of the membrane and reducing transmembrane flow rate. According to aspects of the invention, at least one aspect includes reducing fouling for live oilfield oils while either downhole or above ground. In all cases, at least one aspect includes leveraging the large cross-flow flow rate so as to continually scour or clean the membrane surface, thereby preventing filter cake build-up and/or clogging of membrane pores by particulates or other moieties in the fluid.

Evidence of Fouling, e.g., Filter-Cake Buildup

Figure 9:
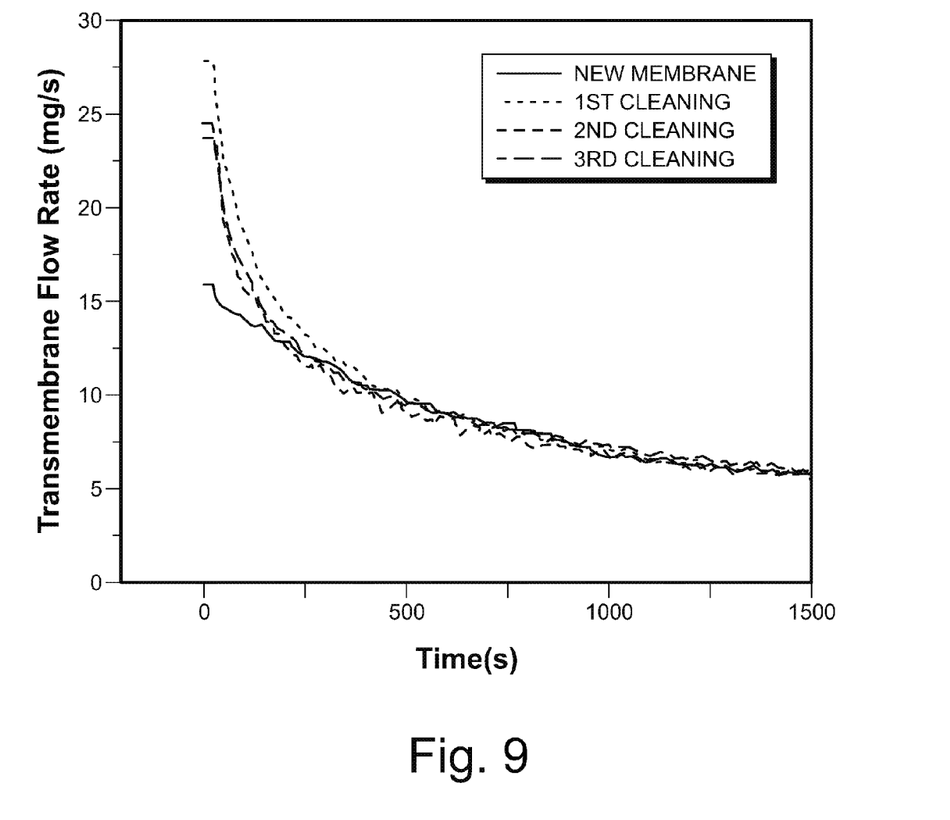
FIG. 9 is a shows a transmembrane flow rate as a function of time for a simulated dead oil which consists of a mixture of Mexican heavy oil and hexadecane according to another aspect of the present invention.
Figure 10:
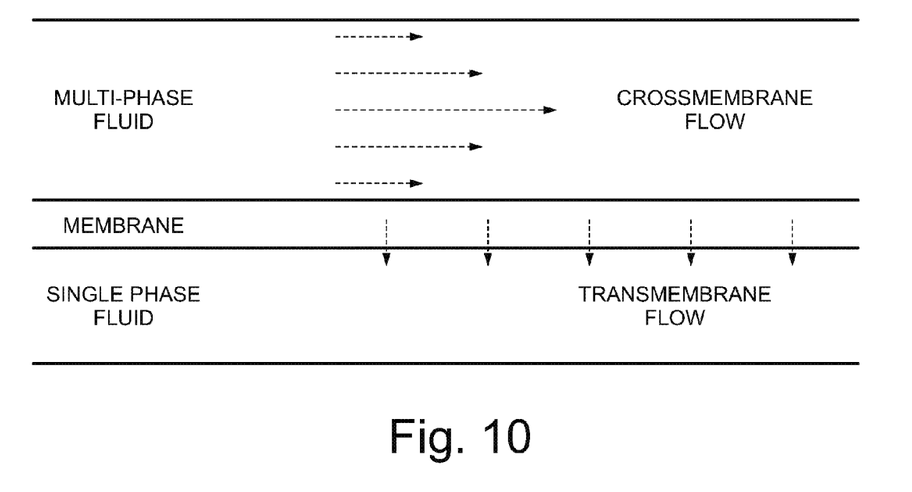
FIG. 10 is a shows the multiphase fluid orientation to the membrane along with showing the cross-membrane flow, trans-membrane flow and single phase fluid in accordance with at least one embodiment of the invention.
Figure 11:
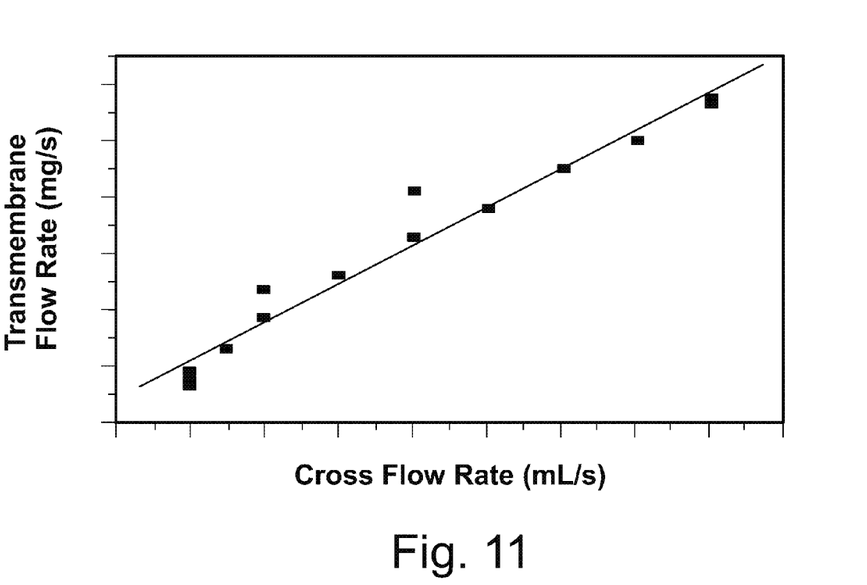
FIG. 11 illustrates the trans-membrane flow rate with time in accordance with at least one embodiment of the invention.

Referring to FIGS. 9-11, FIG. 9 shows a transmembrane flow rate as a function of time for a simulated dead oil which consists of a mixture of Mexican heavy oil and hexadecane. For example, it is noted that this pattern has been identified for a variety of dead oils as well as other fluids possessing fine particules and/or particulates including diesel. FIG. 9 shows that or each curve the transmembrane flow rate can be seen to decrease with time as a filter cake builds up on the membrane. For example, FIG. 10 shows the build-up of the filter cake that occurs as fluid is drawn through the membrane leaving behind moieties, particulates, and fines that are larger than the pore size of the membrane, e.g., membrane fouling. This filter cake can be gently removed from the membrane surface after operation and the mating high pressure enclosure with a gloved hand and the test was repeated with the same membrane. Once again, the transmembrane flow rate started off high (red curve) and decreased with overtime as a new filter cake was produced. This process was repeated two more time (blue and green curves) so as to confirm the results. From these experiments, we concluded that the reduction of the filter-cake was essential for maintaining a transmembrane flow rate, according to at least one aspect of the invention. FIG. 11 illustrates the above noted concepts relating to minimizing fouling of the membrane.

Single Stage

Still referring to FIG. 9 and the flow rate and channel plate geometry, it is note that in some implementations the operator has the freedom to choose the cross membrane flow rate. In this case, it is observed that the highest crossflow flow rates yield the slowest build-up of the filter cake and hence the most effective use of the microfluidic separator. The red and the black curves in the graph below compare the transmembrane flow rate vs time for two different crossflow flowrates (29 and 7 mL/s respectively). It can be seen that that the transmembrane flow rate is highest when the cross membrane flow rate is highest.

Properly designed, the geometry of the channel plate appears to play a strong role as well. The channel plate is the plate that pushes against the membrane on the high pressure side in which there is cross membrane flow. The channel plate may also have a geometry shape approximate to a serpentine pattern, whereby increasing an average shear rate reduces the fouling on the membrane. It is possible the channel plate or the channel could have at least one non-linear surface, at least one corrugated surface, at least two linear surfaces separated by a non-linear surface or some combination thereof, so as to assist in reducing fouling of the membrane. Further, it is noted that there may be more than one channel plate.

By comparing the transmembrane flow rates for two different channel plate designs, one, with several channels in parallel and another, where there is a single long channel that winds about in a serpentine pattern. It was noted that for a given flow rate and channel depth, the transmembrane flow rate is always higher for the serpentine channel plate than for the parallel channel plate as we are reducing the build-up of fouling material with the serpentine channel plate pattern. For the parallel channel plate the average fluid velocity and average shear rate on the membrane surface is lower, thereby decreasing the ability of the fluid to scour and clean the membrane surface.

FIG. 11 shows that the transmembrane flow rate can be directly correlated with the crossflow flow rate in a particulate laden oil flow.

Channel Size or Channel Plate Size

According to certain applications, the crossflow can be fixed or limited and the microfluidic separator needs to be optimized to maximize the transmembrane flow rate requiring a minimization of filter cake build-up. Further, the channel size can be chosen to be sized enough that the average shear rate is high and the membrane surface is swept clean of filter cake but sized accordingly enough so that the crossmembrane pressure drop does not exceed the capillary breakthrough pressure of the membrane.

Surface Corrugations

It is possible in some circumstances it may be advantageous to encourage lateral mixing of the fluid while being circulated about the membrane surface. Such lateral mixing can be accomplished by plate corrugations, which introduces flow in the channel perpendicular to the principle flow direction. Such corrugations would most likely be approximately half the channel depth and of a periodicity similar to the channel width to maximize the lateral flow disturbance. Turbulence can also be induced to encourage lateral mixing, either by increasing the flow Reynolds number or by changing the channel geometry to decrease the critical Reynolds number for turbulent flow, or by increasing the roughness of the channel surface. For a fixed flow rate, some of these geometry changes will produce both greater shear and higher Reynolds number—such as uniformly shrinking the cross sectional area—but corrugations and surface roughness will decrease shear rate at the wall. In these cases, the desirability and scale of these modifications must be assessed based on the expected flow rates, particulate size, and fluid properties.

Dual or Multiple Stage

Further improvement may be possible with a multi-stage filtration approach. In such an implementation, a first microfluidic separator stage would be used to remove particulates in the fashion of a classic filter. In this case, one would not need to maintain the transmembrane pressure below that of a capillary pressure as the filter would be used exclusively for particulate elimination. This staged technique may help reduce the buildup of mud and larger particles on low permability filters used for the final particulate reduction or phase extraction.

One or more embodiments of the present invention have been described. Nevertheless, it will be understood that various modifications may be made without departing from the spirit and scope of the invention. It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A fluid separation method for performing fluid analysis, the fluid separation method comprising:
providing a structure with a fluid analyzer and a power supply;
using a substrate for receiving a fluid flow stream of a multiphase mixture through a fluid sample inlet, wherein the substrate interconnects with the structure; and
providing a porous membrane disposed across the fluid sample inlet for separating a fluid of interest from the multiphase mixture, wherein the fluid flow stream of the multiphase mixture has a shear rate that prevents a fouling of the porous membrane;
wherein the substrate includes fabricated channels, such that the fabricated channels are arranged substantially tangent to the fluid stream downstream of the porous membrane.

2. The fluid separation method according to claim 1, wherein the fluid flow stream is positioned within at least one channel of the substrate such that the fouling is minimized by one of a size of the at least one channel, at least one corrugated surface of the at least one channel, a specific shear rate or some combination thereof.

3. The fluid separation method according to claim 2, wherein the shear rate is determined by a flow rate of the fluid flow stream in the at least one channel along with a size of the at least one channel.

4. The fluid separation method according to claim 2, further comprising inserting the membrane and the structure into a subterranean oilfield environment.

5. The fluid separation method according to claim 1, wherein the at least one channel plate has a geometry shape approximate to a serpentine pattern, whereby increasing an average shear rate reduces the fouling on the membrane.

6. The fluid separation method according to claim 1, wherein the fluid flow stream is in communication with at least one filtration stage prior to the fluid flow stream entering into contact with the membrane, such that the at least one filtration stage includes a first filter that removes at least some particulates from the fluid flow stream.

7. The apparatus according to claim 6, wherein the at least one filtration stage includes a second filtration stage, wherein a second filter uses capillary forces to extract one of an aqueous phase or a hydrocarbon phase.

8. The apparatus according to claim 1, wherein the structure is from the group consisting of one of a wireline conveyed downhole tool, a drill pipe conveyed downhole tool, an oilfield related downhole tool or an other related downhole conveyance device.

9. The fluid separation method according to claim 1, further comprising maintaining a pressure difference across the membrane below a capillary break-through pressure of a non-wetting component of the multiphase mixture.

10. The fluid separation method according to claim 1, wherein the separating comprises part of a measurement while drilling operation, a wireline operation or a permanent production logging operation.

11. The fluid separation method according to claim 10, wherein the separating is done by a surface device for mud sample analysis.

12. The fluid separation method according to claim 10, wherein the separating is done inside a fluid sample bottle.

13. The fluid separation method according to claim 1, wherein the membrane comprises one of a water-repellant, oil-permeable membrane, an oil-repellent, water-permeable membrane, an oil-and-water-repellent or a gas-permeable membrane.

14. The fluid separation method according to claim 1, wherein the separating comprises flowing the liquid of interest from the multiphase mixture through the membrane at a flow rate at least one-to-two orders of magnitude lower than a flow rate of the multiphase mixture passing by the membrane.

15. The fluid separation method according to claim 1, wherein the separating comprises passing the liquid of interest from the multiphase mixture through the membrane and preventing the membrane from fouling without back-flushing.

16. The fluid separation method according to claim 1, further comprising maintaining substantially equal pressure drop across an entire area of the membrane.

17. The fluid separation method according to claim 16, wherein maintaining substantially equal pressure comprises supporting the membrane with the fabricated channels.

18. The fluid separation method according to claim 17, wherein the fabricated channels is a microseive comprised of an H-fractal fluid channel configuration.

19. The fluid separation method according to claim 1, wherein the separating comprises part of a measurement while drilling operation, a wireline operation, a permanent production logging operation, a mud logging operation, or a laboratory analysis.

20. The fluid separation method according to claim 1, wherein the fluid analyzer includes measuring one or more properties of the fluid such as rheological properties.

21. The fluid separation method according to claim 1, wherein the fluid analyzer includes measuring one or more properties of the fluid such as fluid composition.

22. The fluid separation method according to claim 1, wherein the fluid analyzer includes measuring one of a surface tension of the fluid, a standard pressure volume temperature (PVT) analysis or other thermodynamic phase measurements.

23. The fluid separation method according to claim 1, wherein the fluid analyzer includes measuring one or more properties of the fluid such as a pressure, a density, a viscosity, a temperature or some combination thereof.

24. An apparatus, comprising:
a microfluidic device disposed within a structure, the microfluidic device comprising:
a porous membrane for separating a multiphase mixture in a fluid flow stream, wherein a pressure difference across the porous membrane is maintained below a capillary break-through pressure of a nonwetting fluid phase present in the multiphase mixture;

at least one channel plate positioned proximate to the membrane, the at least one channel plate configured to direct the fluid flow stream along the porous membrane;

wherein the porous membrane is arranged substantially tangent to an intended fluid flow direction of the multiphase mixture present in the fluid flow stream; and a microsieve is structured and arranged adjacent to and downstream of the membrane and includes a capillary fluid separator having microfabricated channels arranged substantially tangent to the fluid flow stream.

25. The apparatus according to claim 24, wherein the channel plate includes at least one channel and the fluid flow stream within the at least one channel has a shear rate, wherein a specific average shear rate of the shear rate prevents a fouling on the membrane, wherein fouling includes
a filter cake build up,
a clogging of a pore of the membrane, or
both.

26. The apparatus according to claim 25, wherein the fouling is minimized by a determined shear rate, a size of the at least one channel, at least one corrugated surface of the at least one channel or some combination thereof.

27. The apparatus according to claim 26, wherein the determined shear rate is calculated by a flow rate of the fluid flow stream in the at least one channel along with a size of the at least one channel.

28. The apparatus according to claim 25, wherein the at least one channel includes at least one non-linear surface, at least one corrugated surface, at least two linear surfaces separated by a non-linear surface or some combination thereof.

29. The apparatus according to claim 25, wherein the at least one channel is shaped as one of a uniform shape, a non-uniform shape or a wave-type shape.

30. The apparatus according to claim 24, wherein the at least one channel plate has a geometry shape approximate to a serpentine pattern, whereby increasing the average shear rate so as to reduce the fouling on the membrane.

31. The apparatus according to claim 24, wherein the fluid flow stream is in communication with at least one filtration stage prior to the fluid flow stream entering into contact with the membrane, such that the at least one filtration stage includes a first filter that removes at least some particulates from the fluid flow stream.

32. The apparatus according to claim 31, wherein the at least one filtration stage includes a second filtration stage, wherein the second filtration stage has a second filter that uses capillary forces to extract one of an aqueous phase or a hydrocarbon phase.

33. The apparatus according to claim 24, wherein the structure is from the group consisting of one of:
a wireline conveyed downhole tool,
a drill pipe conveyed downhole tool,
an oilfield related downhole tool, or
another related downhole conveyance device.

34. The apparatus according to claim 33, wherein the structure is a submersible housing surrounding the microfluidic device.

35. The apparatus according to claim 24, wherein one or more mesh device is positioned proximate the at least one channel plate.

36. The apparatus according to claim 24, wherein the structure is an uphole device.

37. The apparatus according to claim 24, wherein the microfluidic device comprises a sample manipulation/analysis module or a chip.

38. The apparatus according to claim 37, wherein the sample manipulation/analysis module or the chip is configured to measure includes measuring one or more properties of the fluid such as rheological properties.

39. The apparatus according to claim 37, wherein the sample manipulation/analysis module is configured to measure one or more properties of the fluid such as fluid composition.

40. The apparatus according to claim 37, wherein the sample manipulation/analysis module is configured to measure one of: a surface tension of the fluid; a standard pressure volume temperature (PVT) analysis; or other thermodynamic phase measurements.

41. An apparatus, comprising:
a housing positioned in a downhole oilfield tool, the housing having a fluid flow stream;
a microfluidic device positioned in the housing, the microfluidic device comprising:
a porous membrane for separating a multiphase mixture in the fluid flow stream, wherein a pressure difference across the porous membrane is maintained below a capillary break-through pressure of a nonwetting fluid phase present in the multiphase mixture;
at least one channel plate positioned proximate to the membrane, the at least one channel plate configured to direct the fluid flow stream along the porous membrane;
wherein the porous membrane is arranged substantially tangent to an intended fluid flow direction of the multiphase mixture present in the fluid flow stream; and
a microsieve structured and arranged adjacent to and downstream of the porous membrane and includes a capillary fluid separator having microfabricated channels arranged substantially tangent to the fluid flow stream.

* * * * *